US010342232B1

(12) United States Patent
Brothers et al.

(10) Patent No.: US 10,342,232 B1
(45) Date of Patent: Jul. 9, 2019

(54) IODINATED POLYMERS FOR BIOLOGICAL AGENT DEFEAT

(71) Applicant: Department of the Navy, Washington, DC (US)

(72) Inventors: Robert Carl Brothers, Potomac, MD (US); Rebecca Martin Wilson, Alexandria, VA (US); Michelle Pantoya, Lubbock, TX (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/350,264

(22) Filed: Oct. 24, 2018

(51) Int. Cl.

| | |
|---|---|
| ***A01N 37/18*** | (2006.01) |
| ***C08G 69/04*** | (2006.01) |
| ***A01N 25/10*** | (2006.01) |
| ***C08G 69/26*** | (2006.01) |
| ***C06B 45/10*** | (2006.01) |

(52) U.S. Cl.
CPC ............ *A01N 37/18* (2013.01); *A01N 25/10* (2013.01); *C06B 45/10* (2013.01); *C08G 69/04* (2013.01); *C08G 69/26* (2013.01)

(58) Field of Classification Search
CPC ........ A01N 37/18; A01N 25/10; C08G 69/04; C08G 69/26; C06B 45/10
See application file for complete search history.

(56) References Cited

U.S. PATENT DOCUMENTS

| | | | | |
|---|---|---|---|---|
| 2,247,880 A * | 7/1941 | Guerbet | ............. | A61K 49/0438 252/478 |
| 3,154,612 A | 10/1964 | Parczewski | | |
| 5,663,432 A | 9/1997 | Villa et al. | | |
| 5,693,311 A | 12/1997 | Petta et al. | | |

OTHER PUBLICATIONS

Mattern, Direct Aromatic Periodination, 1983, J. Org. Chem., 49, 3051-3053. (Year: 1983).*

Jouet et al, Surface Passivation of Bare Aluminum Nanoparticles Using Perfluoroalkyl Carboxylic Acids, 2005, Chem. Mater., 17, 2987-2996. (Year: 2005).*

Clark et al, The aluminium and iodine pentoxide reaction for the destruction of spore forming bacteria, 2010, Phys. Chem. Chem. Phys., 12, 12653-12657. (Year: 2010).*

McCollum et al, Activating Aluminum Reactivity with Fluoropolymer Coatings for Improved Energetic Composite Combustion, 2015, ACS Appl. Mater. Interfaces, 7, 18742-18749. (Year: 2015).*

* cited by examiner

*Primary Examiner* — Trevor Love
(74) *Attorney, Agent, or Firm* — Fredric J. Zimmerman

(57) ABSTRACT

A binder, and related processes, has been developed for biological agent defeat formulations. This highly iodinated binder is based on the polymer polyethylene tetraiodoterephthalamide. The materials have been formulated with metal fuel particles, such as aluminum, and various oxidizers, such as metal oxides. The binder-thermite composites may be actuated to initiate oxidation, therein generating heat. Upon thermal decomposition of these materials, iodine, a biocide, is released allowing for sterilization of biological agents.

14 Claims, 10 Drawing Sheets terephthalic acid
tetraiodoterephthalic acid
tetraiodoterephthalic acid
tetraiodoterephthaloyl chloride
tetraiodoterephthaloyl chloride
polyethylene tetraiodoterephthalamide dissolving terephthalic acid in 20% fuming sulfuric acid in a reaction flask, wherein the flask is vented to a sulfuric acid bubbler, stirred, and heated to a temperature of 100 C;

adding iodine to the reaction flask, and incrementally raising the temperature to 125 C for 30 min, wherein the flask is wrapped in foil and the temperature is increased to 150 C for 15 min, 170 C for 15 min, and 190 C for 6 hrs;

allowing the reaction mixture to cool overnight;

pouring the mixture into ice cold water, washing the flask therein forming a slurry having a pink solid, which is collected by vacuum filtration, wherein the pink solid is impure TIPA;

purifying the TIPA by dissolving it in aqueous KOH to a pH of 10, vacuum filtering, adding NaHSO3 to the filtrate, therein causing the TIPA to precipitate by the addition of concentrated HCl acid to a pH of 1, vacuum filter the precipitate to dryness and allowing it to air dry overnight;

removing any remaining impurity by triturating the TIPA with acetone at room temperature and in hot methanol, and then vacuum filtering until the TIPA is a white solid at 45% yield.

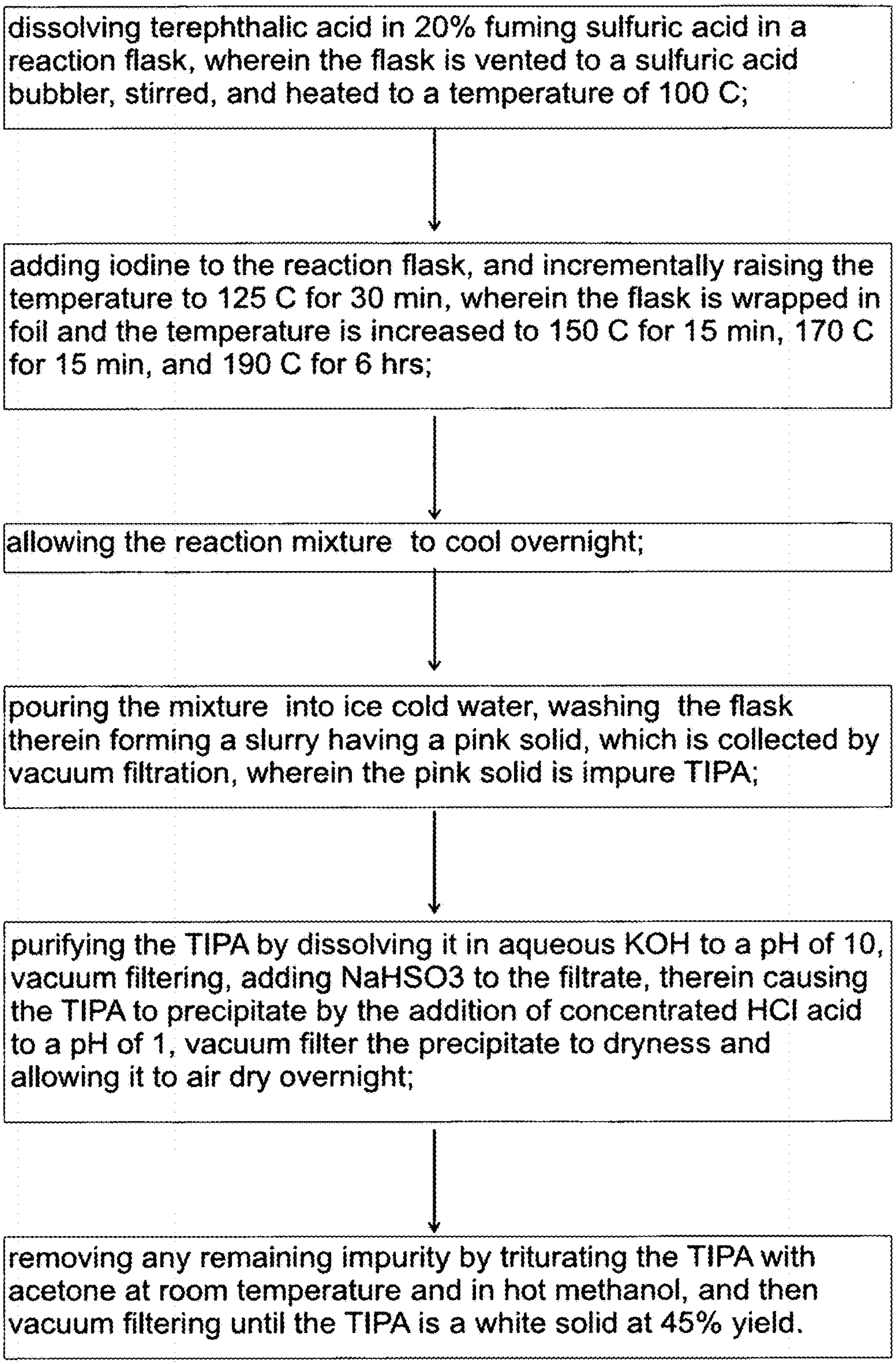

*FIG. 2a* adding tetraiodoterephthalic acid and an excess thionyl chloride to a dried Schlenk flask connected to a reflux condenser and under argon atmosphere;

stirring and heating the Schlenk flask for 6 hrs at 100 °C;

removing by evaporation any unreacted thionyl chloride leaving impure tetraiodoterephthaloyl chloride;

dissolving the impure tetraiodoterephthaloyl chloride in anhydrous tetrahydrofuran (THF);

filtering the dissolved tetraiodoterephthaloyl chloride using a cannula tube;

evaporating the THF leaving a tan solid; and drying by high vacuum the tetraiodoterephthaloyl chloride resulting in a 75% yield.

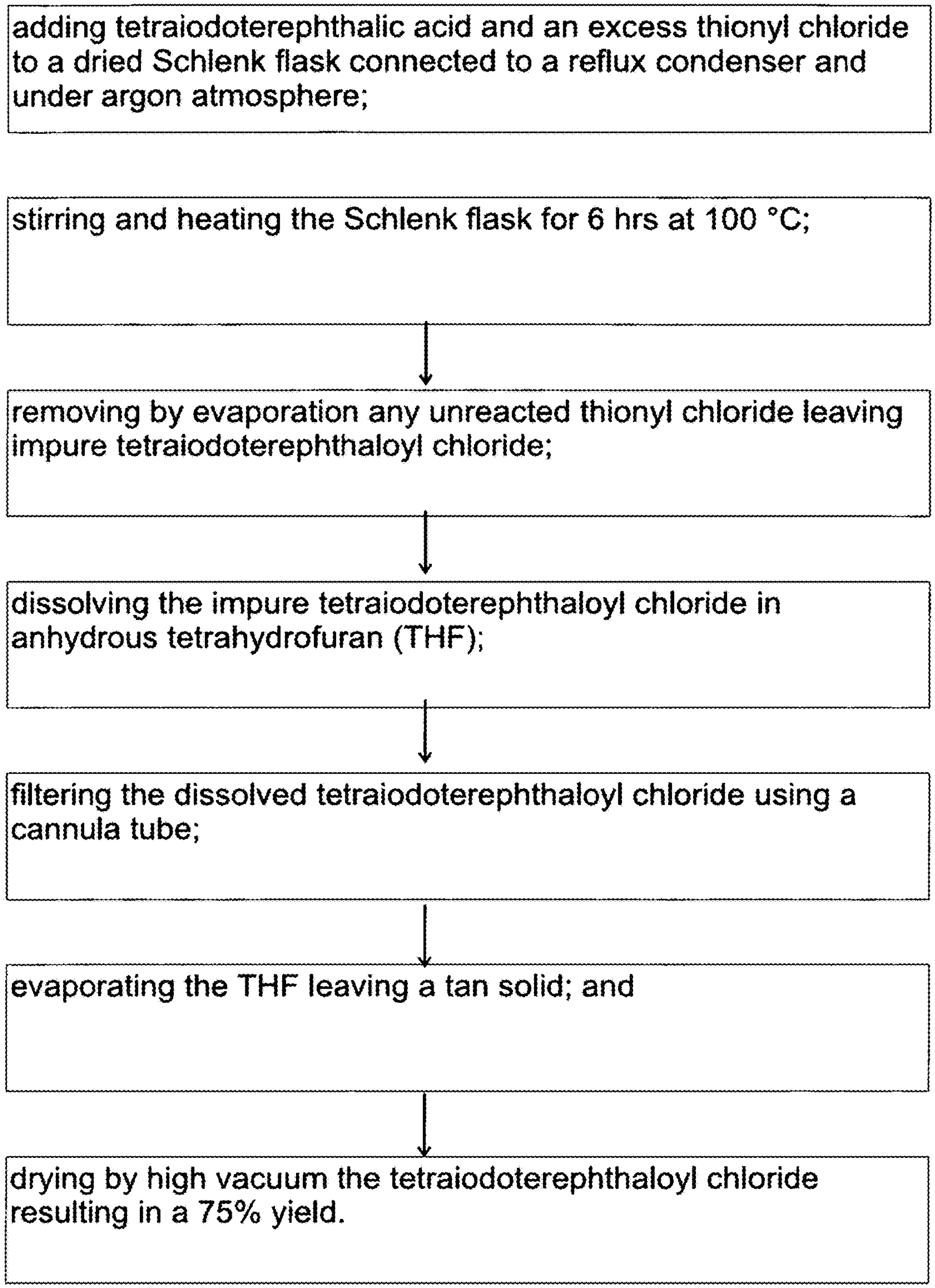

(TIPC)

IODINATED POLYMERS FOR BIOLOGICAL AGENT DEFEAT

STATEMENT OF GOVERNMENT INTEREST

The invention described herein may be manufactured and used by or for the Government of the United States of America for Governmental purposes without the payment of any royalties thereon or therefore.

FIELD OF THE INVENTION

The invention relates generally to biocide-containing binders for biological agent defeat formulations. More particularly to a novel iodinated polymer that provides antimicrobial properties, via iodine release, upon thermal decomposition. Additionally, the iodinated polymer acts as a binder, encasing fuel and oxidizer in biological agent defeat formulations. By joining the iodinated binder with a metal fuel, such as aluminum, and an oxidizer, such as a metal oxide or perfluorinated material, high burning temperatures can be combined with iodine release to enhance biocidal properties.

BACKGROUND OF THE INVENTION

Conventional technology teaches that nano aluminum (Al) particles passivated by a perfluorinated carboxylic acid coating exhibit enhanced burning compared to nanoparticles with an aluminum oxide coating. The typical aluminum oxide coating on an aluminum particle of any size is 1.7-6.0 nm thick. For nano aluminum particles, this accounts for approximately 45% of the total mass, leading to a significant inhibition of the burning rate because almost half of the material is non-reactive. By passivating the aluminum surface with a carboxylic acid, the bulk of the aluminum nanoparticle is available for oxidation chemistry. Additionally, the use of a perfluorinated carboxylic acid incorporates a very powerful oxidizer within an intimate setting with the metal fuel. The oxidation of aluminum (Al) to $AlF_3$ (13.31 kcal/g) is far more energetic than the oxidation to $Al_2O_3$ (7.4 kcal/g). This combination of a strong oxidizer in close proximity and an abundant highly available fuel allow for the enhanced burning rate reported by Jillian M. Horn et. al. Formulations with the inventive technology used micron sized aluminum instead of nano because the larger particles offer longer burn times and the oxide layer becomes a very small percentage of the overall particle, such that it does not impede combustion.

Additional conventional technology teaches electrophilic aromatic iodination is effected using fuming sulfuric acid, powdered iodine, and heat. Various benzene derivatives have been polyiodinated and used as contrast agents during X-ray radiographies. These compounds are substituted by 4 or 5 iodine atoms. One of the compounds is tetraiodoterephthalic acid and its amide derivative, thus inspiring a synthesis for the inventive technology.

Further conventional technology teaches processes for the conversion of carboxylic acids to their analogous acid chlorides using thionyl chloride.

Further conventional technology teaches processes for the polymerization of polyamides from acid chlorides and amines.

Typically, in conventional technologies the iodine pentoxide is not particularly stable upon exposure to moisture and decomposes into iodic acid. The acid then reacts and causes the binder to decompose in current formulations. This result is not desirable, and the inventors' technology resolves these deficiencies and provides something more stable. The inventive material contains organic iodine attached along the aromatic carbon backbone of the polymer, which, with sufficient flexibility, also may function as a binder. Therefore, the inventive technology is a replacement of both the binder and iodine pentoxide in biological agent defeat formulations.

SUMMARY OF THE INVENTION

The invention is a novel highly iodinated binder that is based on the polymer polyethylene tetraiodoterephthalamide (PETITA) and analogs thereof. This material offers two major advantages for biological agent defeat formulations because it can act as both a biocide source and a binder. First, the material can release biocidal iodine upon thermal decomposition. Thermal decomposition can occur from indirect heating, such as a hot plate, or direct heating, such as explosively initiated combustion. Second, the material can act as a binder encasing biological agent defeat formulations. Pressed formulations can be prepared because this material is a compactable white powder that can hold fuel and oxidizer together.

The invention includes biological agent defeat formulations with the iodinated binder. By combining a metal fuel, such as aluminum, with a sufficient oxidizer, such as a metal oxide or perfluorinated molecule, high reaction temperatures and long burn times can be achieved. Aluminum is oxidized by metal oxides and sources of fluorine to release heat and facilitate combustion. These polymer-thermite mixtures will provide sufficient energy to thermally sterilize a biological agent, and thermally decompose the iodinated binder, which will release iodine as a secondary biological sterilization. This two-step sterilization approach will ensure sufficient biological agent defeat.

An additional aspect of the invention includes formulations with the iodinated binder that are designed to burn at lower temperatures. In some biological agent defeat applications, high burn temperatures and long burn times may be undesirable. Therefore, thermally decomposing the polymer at a lower temperature may be required, making iodine release the primary biological sterilization step for agent defeat. This can be achieved by varying the types and amounts of fuel and oxidizer in the formulation.

The invention further includes a process for synthesizing PETITA and its iodinated binder analogs; and a method of preparing formulations by combining it with a metal fuel, such as aluminum particles, and an oxidizer, such as a metal oxide or a perfluorinated carboxylic acid.

An object of the invention is to provide a highly iodinated binder with the desired mechanical properties for use in an agent defeat formulation.

A second object of the invention is that the polymer utilizes relatively common starting materials in part to minimize eventual production costs.

A third object of the invention is that the process for synthesizing PETITA and analogs thereof has a relatively few number of steps in the synthesis.

A fourth object of the invention is that the aluminum fuel particles are in the micron size range, versus the nanometer size range to lengthen burn times, thus improving the biocidal capabilities.

A fifth object of the invention is that the highly iodinated binder may be part of a formulation with a metal fuel other than aluminum.

A final object of the invention is that the highly iodinated binder may be part of a formulation with various oxidizers, such as perfluorinated compounds, metal oxides, or iodine pentoxide.

BRIEF DESCRIPTION OF THE DRAWINGS

The foregoing invention will become readily apparent by referring to the following detailed description and the appended drawings in which:

FIG. 2*a* is a flow diagram of the process for synthesizing tetraiodoterephthalic acid;

FIG. 2*b* is a flow diagram of the process for synthesizing tetraiodoterephthaloyl chloride;

DETAILED DESCRIPTION OF THE INVENTION

The invention is a new highly iodinated binder, based on the polyethylene tetraiodoterephthalamide (PETITA) polymer. As shown in Rx 3 of FIG. 1, the polymer is formed by the condensation reaction of two monomers, tetraiodoterephthaloyl chloride and ethylene diamine. The polymerization occurs in a relatively polar solvent NMP ((N-Methyl-2-pyrrolidone). The TEA (triethylamine) is an organic base that neutralizes HCl, which is formed as an amine group from ethylene diamine reacts with the tetraiodoterephthaloyl chloride.

Figure 1:
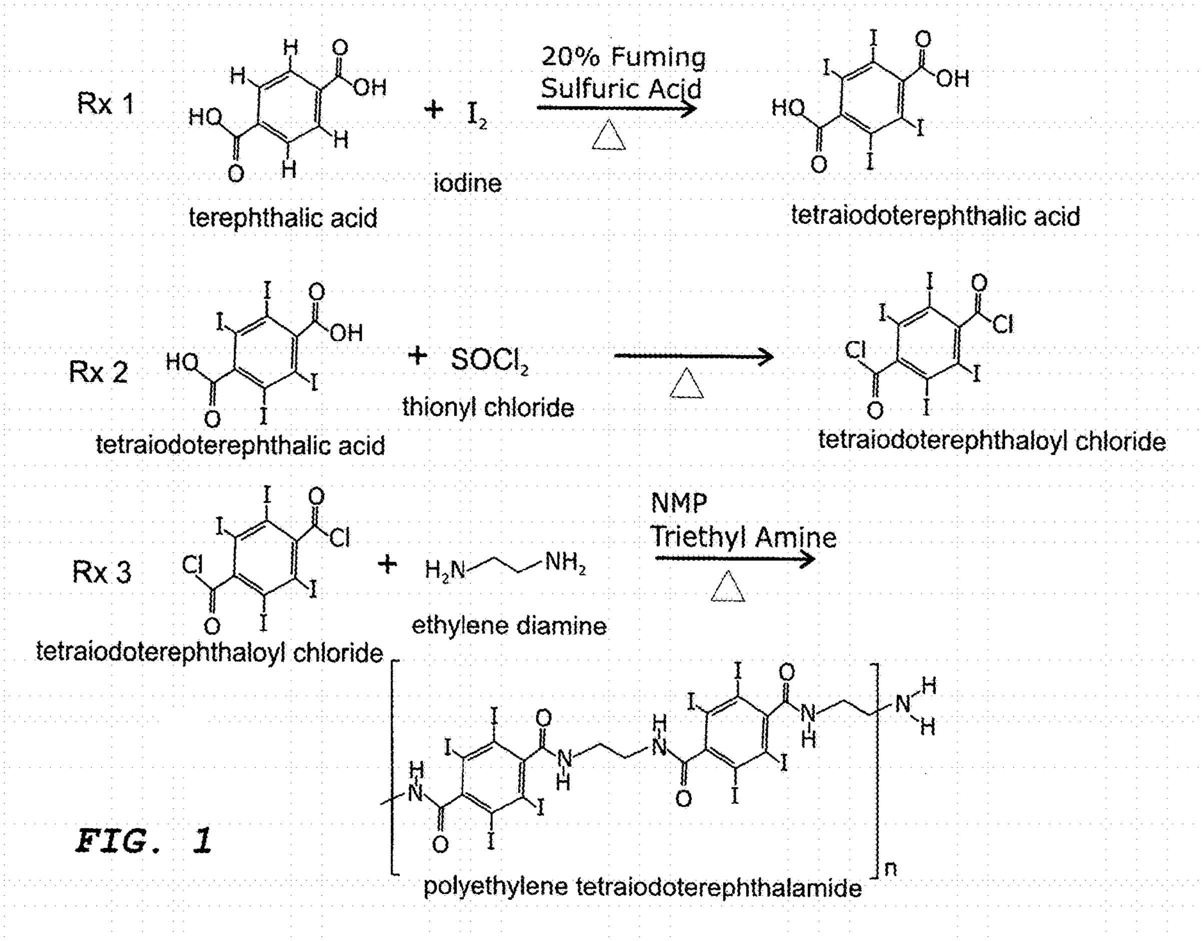
FIG. 1 illustrates the reaction sequence for the synthesis of PETITA, where (Rx 1) terephthalic acid is periodinated to tetraiodoterephthalic acid with heat and time in fuming sulfuric acid and iodine. In (Rx 2), tetraiodoterephthalic acid is converted into tetraiodoterephthaloyl chloride by reacting the tetraiodoterephthalic acid with an excess of thionyl chloride, and in (Rx 3) polyethylene tetraiodoterephthalamide (PETITA) is formed by reacting a stoichiometric amount of tetraiodoterephthaloyl chloride dissolved in NMP (N-Methyl-2-pyrrolidone) and TEA (triethylamine) with a stoichiometric amount of ethylene diamine dissolved in NMP.

The periodation of terephthalic acid, as shown in Rx 2 of FIG. 1 illustrates just how stable terephthalic acid is, as the reaction takes place over many hours in 20% fuming sulfuric acid. The 20% refers to the amount of dissolved $SO_3$ in the sulfuric acid.

Conversion of tetraiodoterephthalic acid (TIPA) to the tetraiodoterephthaloyl chloride (TIPC) is shown Rx 2 of FIG. 1. The reaction is facilitated by the solubility of the product (TIPC) in thionyl chloride as compared to the insoluble starting material (TIPA), thus allowing for ease of reaction monitoring.

Embodiments of the experimental procedures are described below.

a. (Actual) Experimental Procedure for Synthesizing Tetraiodoterephthalic Acid (TIPA):

To a round bottom flask was added terephthalic acid (2.49 g, 14.94 mmol) and 20% fuming sulfuric acid (40.00 mL, 275 mmol). The reaction flask was vented to a sulfuric acid bubbler and allowed to stir at 100° C. until the terephthalic acid dissolved (approximately 30-45 min). Iodine (10.00 g, 39.40 mmol) was added to the reaction flask and the temperature increased to 125° C. for 30 min. The reaction setup was then wrapped in foil and the temperature was increased to 150° C. for 15 min, 170° C. for 15 min, and finally 190° C. The reaction stirred at 190° C. for 6 hrs. The reaction mixture was cooled overnight. The reaction mixture was then poured into ice cold water and the flask was washed with water two times. The combined aqueous layers were vacuum filtered until a chunky pink solid was obtained. The solid was dissolved into aqueous KOH to a pH of 10 and the liquid was vacuum filtered. $NaHSO_3$ (0.25 g, 2.40 mmol), which is a weaker acid, was added to the filtrate and the product was precipitated using concentrated hydrochloric acid to a pH of 1. The precipitate was vacuum filtered to dryness and allowed to air dry overnight on a watch glass. The light pink solid was then triturated by pulverization in acetone followed by vacuum filtration, and the remaining solid was washed with portions of acetone until the filtrate ran clear and colorless. The white solid was crushed up in hot methanol and vacuum filtered, then washed with small portions of hot methanol (approximately 2-3 washings). The white solid was dried on high vacuum to give tetraiodoterephthalic acid in 45% yield (4.54 g, 6.78 mmol). 13C NMR: δ 170, 150, 108 ppm. LCMS: 624 (MW-$CO_2$) m/z. IR: 2900, 1703 $cm^{-1}$.

b. (Actual) Experimental Procedure for Synthesizing Tetraiodoterephthaloyl Chloride (TIPC):

To an oven dried Schlenk flask under argon atmosphere was added tetraiodoterephthalic acid (4.50 g, 6.72 mmol) and thionyl chloride (15.00 mL, 301.50 mmol). The reaction flask was connected to a reflux condenser and allowed to stir at 100° C. under a positive flow of argon for 6 h. The excess thionylchloride was removed by evaporation. The crude material was dissolved in anhydrous tetrahydrofuran and canula filtered. Solvent is removed by evaporation. The tan solid was dried on high vacuum to give tetraiodoterephthaloyl chloride in 75% yield (3.58 g, 5.07 mmol). $^{13}$C NMR: δ 168, 150, 108 ppm. LCMS: 742 (MW+$^{37}$Cl), 740 (MW+$^{35}$Cl) m/z. IR: 1755 $cm^{-1}$.

c. (Actual) Experimental Procedure for Synthesizing Polyethylene Tetraiodoterephthalamide (PETITA):

To an oven dried Schlenk flask under argon atmosphere was added tetraiodoterephthaloyl chloride (1.01 g, 1.43 mmol), NMP (2.00 mL, 20.75 mmol), TEA (0.20 mL, 1.43 mmol), and ethylene diamine (0.12 mL, 1.48 mmol) dissolved in NMP (2.00 mL, 20.75 mmol). The reaction mixture was allowed to stir overnight at room temperature with a positive flow of argon. The reaction mixture was diluted with water and vacuum filtered. The solid was washed with ethanol and diethyl ether. The light yellow solid was crushed up and dried on high vacuum to give polyethylene tetraiodoterephthalamide in quantitative yield (1.04 g). IR: 3265, 1636, 1547, 1260 $cm^{-1}$.

The process for forming the tetraiodoterephthalic acid includes the following steps as shown in the flow diagram in FIG. 2*a:*

Dissolving terephthalic acid in 20% fuming sulfuric acid in a reaction flask, wherein the flask is vented to a sulfuric acid bubbler, stirred, and heated to a temperature of 100° C.;

Adding iodine to the reaction flask, and incrementally raising the temperature to 125° C. for 30 min, then wrapping the flask in foil and increasing the temperature to 150° C. for 15 min, 170° C. for 15 min, and 190° C. for 6 hrs;

Allowing the reaction mixture to cool overnight;

Pouring the mixture into ice cold water, washing the flask therein forming a slurry having a pink solid, which is collected by vacuum filtration, wherein the pink solid is impure TIPA;

Purifying the TIPA by dissolving it in aqueous KOH to a pH of about 10, vacuum filtering, adding $NaHSO_3$ to the filtrate, therein causing the TIPA to precipitate by the addition of concentrated HCl acid to a pH of about 1, vacuum filter the precipitate to dryness and allowing it to air dry overnight; and Removing any remaining impurity by triturating the TIPA with acetone at room temperature and in hot methanol, and then vacuum filtering until the TIPA is a white solid at 45% yield.

The process for forming the tetraiodoterephthaloyl chloride includes the following steps as shown in the flow diagram in FIG. 2*b.:*

Adding tetraiodoterephthalic acid and an excess thionyl chloride to a dried Schlenk flask connected to a reflux condenser and under argon atmosphere;

Stirring and heating the Schlenk flask for 6 h at 100° C.;

Removing by evaporation any unreacted thionyl chloride leaving impure tetraiodoterephthaloyl chloride;

Dissolving the impure tetraiodoterephthaloyl chloride in anhydrous tetrahydrofuran (THF);

Filtering the dissolved tetraiodoterephthaloyl chloride using a cannula tube;

Evaporating the THF leaving a tan solid; and

Drying the tam solid under high vacuum to give the tetraiodoterephthaloyl chloride in 75% yield.

Figure 2C:
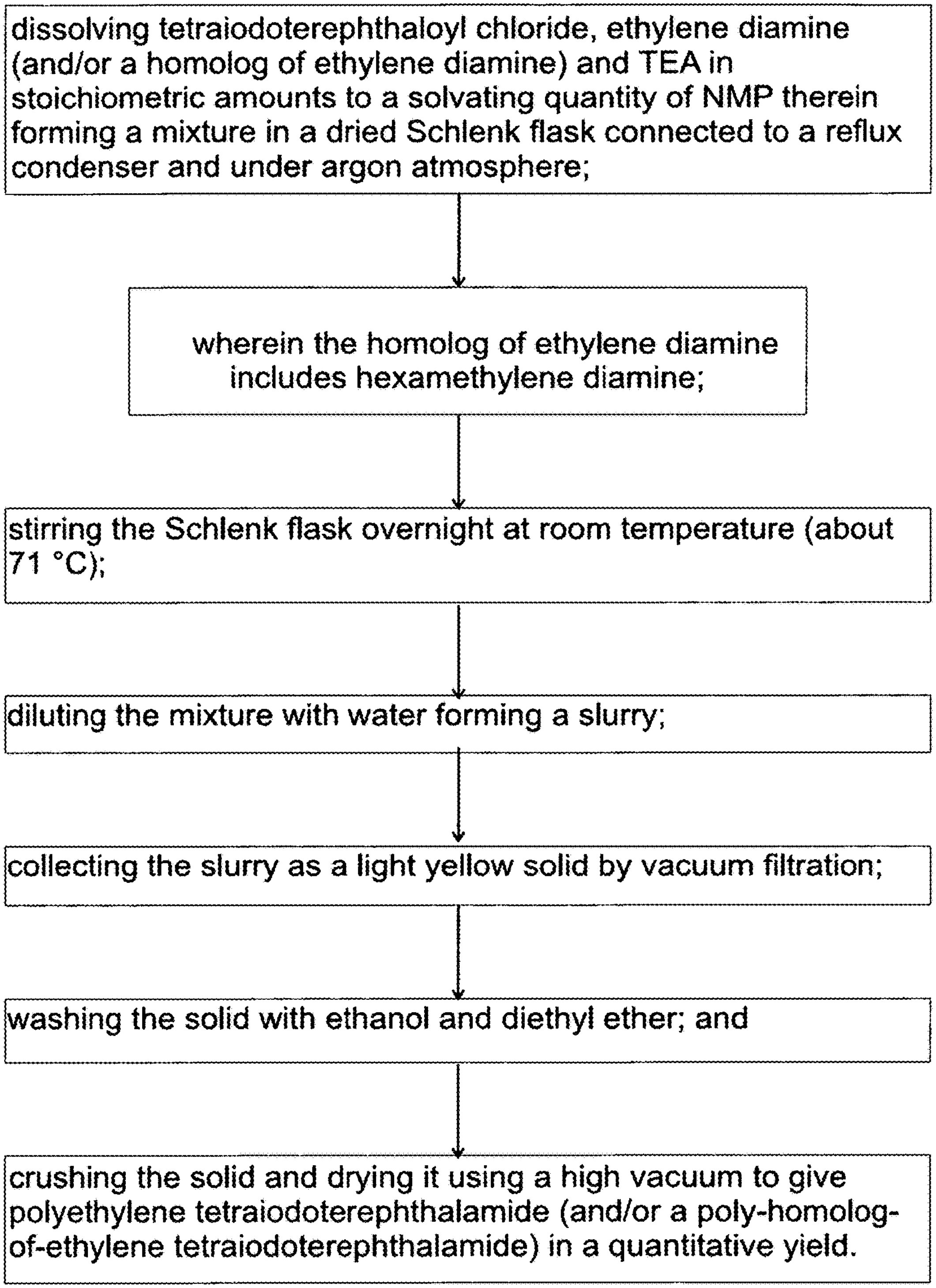
FIG. 2*c* is a flow diagram of the process for synthesizing PETITA and analogs thereof.

The process for forming the polyethylene tetraiodoterephthalamide includes the following steps as shown in the flow diagram in FIG. 2*c.:*

Dissolving stoichiometric amounts of tetraiodoterephthaloyl chloride, ethylene diamine, and TEA into NMP in a dried Schlenk flask under argon atmosphere;

Stirring the Schlenk flask overnight at room temperature;

Diluting the mixture with water to form a slurry;

Collecting the slurry as a light yellow solid by vacuum filtration;

Washing the solid with ethanol and diethyl ether; and

Crushing the solid and drying it using a high vacuum to give polyethylene tetraiodoterephthalamide in a quantitative yield.

Figure 3:
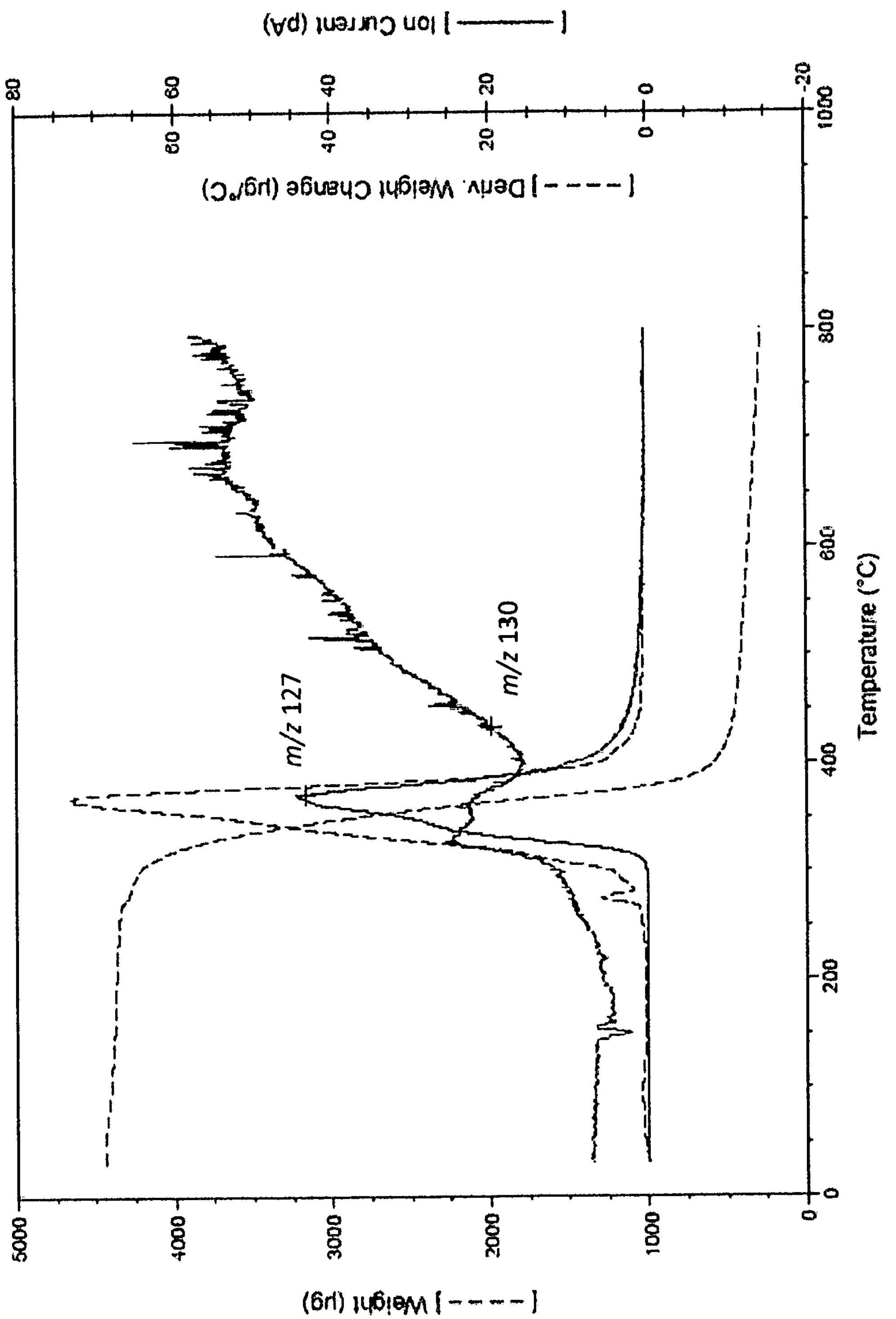
FIG. 3 is the TGA-EGA data for PETITA. At the thermal decomposition temperature of 350° C., the mass spectrometer detects m/z of 127 indicating Iodine release.

Thermogravimetric analysis with evolved gas analysis (TGA-EGA) data of the pure polyethylene tetraiodoterephthalamide polymer is shown in FIG. 3. At the thermal decomposition temperature of 350° C., the mass spectrometer detects m/z of 127 indicating HI release. Follow-up studies with a melting point apparatus indicate the polymer decomposes at 285° C. releasing a purple gas (iodine). The difference in observed decomposition temperatures is likely due to differences in heating rate, as well as differences between the inert gas flow required for TGA-EGA and a melting point apparatus that is open to atmospheric oxygen. This combined information confirms that the polymer does release iodine by a thermal decomposition method.

Metal fuels, such as aluminum, and various oxidizers, such as metal oxides, were added to the previously described polymerization reaction mixture during setup to entrap the particles within the polymer matrix, which produced polymer-metal or polymer-thermite composites.

Figure 4:
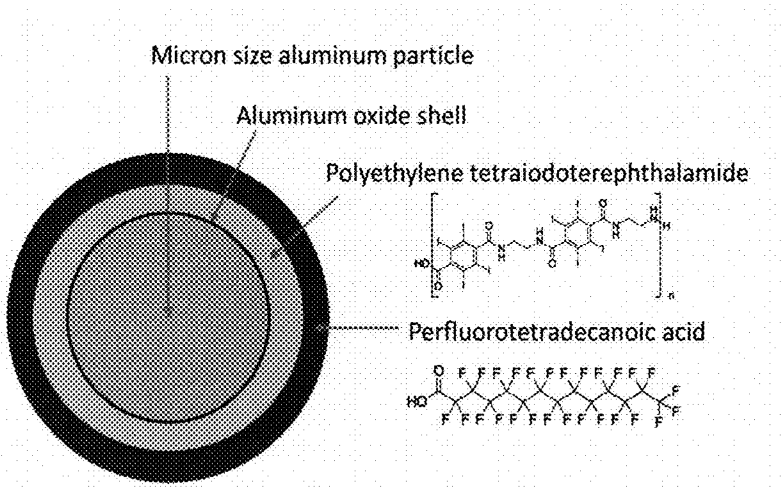
FIG. 4 diagrammatically illustrates a micron sized particle of aluminum having an aluminum oxide surface layer, which is trapped within the polymer matrix of polyethylene tetraiodoterephthalamide (PETITA). This polymer-metal composite has an outer coating of perfluorotetradecanoic acid.

After polymerization, the polymer-metal composites were evaporatively coated with a fluorinated organic material, perfluorotetradecanoic acid. A micron sized particle of aluminum depicting these types of materials is illustrated in FIG. 4. It is shown as a cross-sectional view to illustrate that the core is elemental aluminum (grey layer), while the surface is oxidized to aluminum oxide (black layer). These aluminum particles were trapped within the polymer matrix of polyethylene tetraiodoterephthalamide (yellow layer) during the polymerization reaction. After polymerization, the polymer-metal composites were coated with perfluorotetradecanoic acid (purple layer) by an evaporative process.

Figure 5:
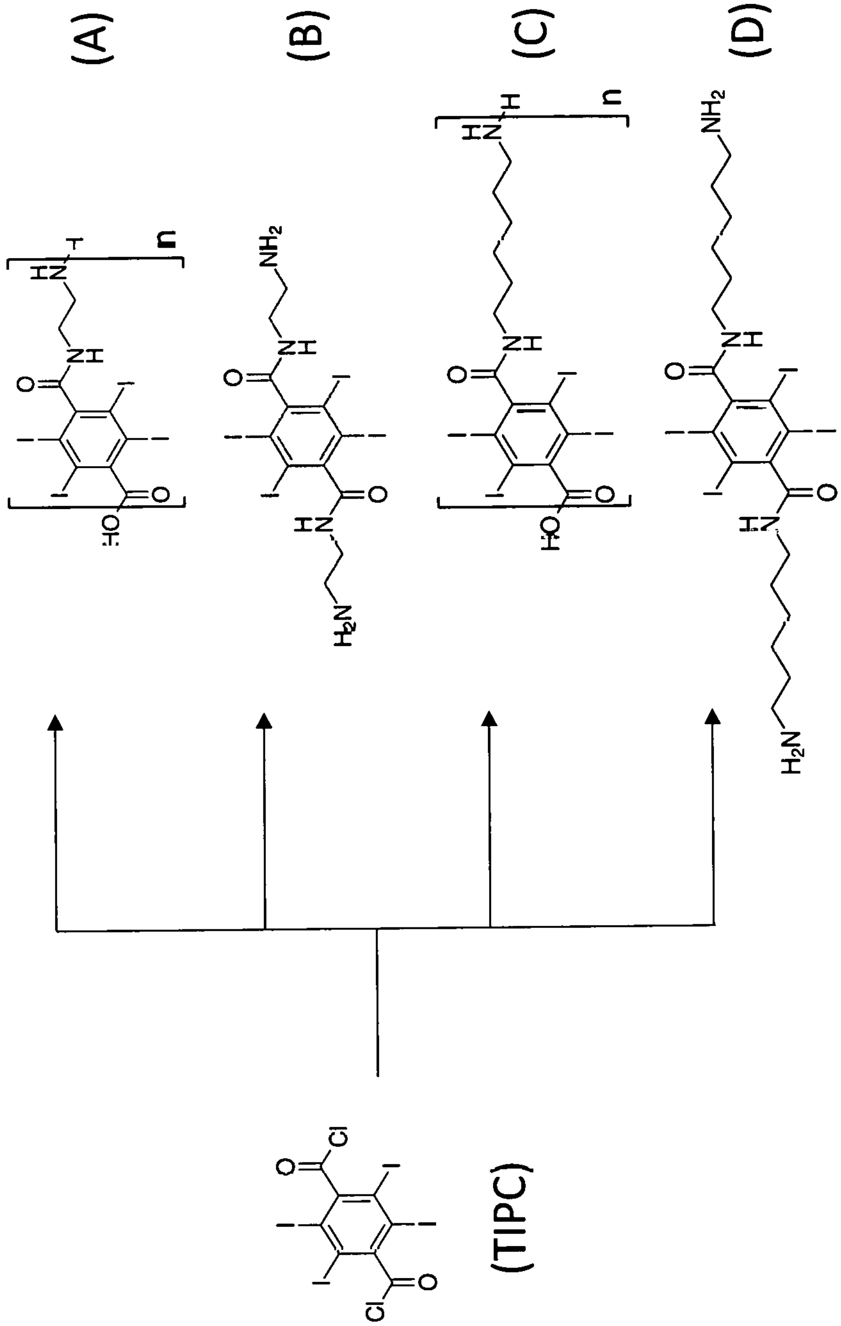
FIG. 5 illustrates the reaction sequence utilizing tetraiodoterephthaloyl chloride for polymerization with various diamines to give different polymers (A & C). Additionally, the polymerization reaction conditions were further modified to select for the trimer products (B and D)

Other diamines, such as hexamethylenediamine (FIG. 5), can react with tetraiodoterephthaloyl chloride to generate other polymer analogs using the previously described polymerization procedure. Tetraiodoterephthanoyl chloride was polymerized with various diamines to give different polymers (FIGS. 5, A & C). Additionally, the polymerization reaction conditions could be used to obtain polymers of shorter lengths, for example, the trimer products (FIGS. 5, B and D) were prepared. Compound D (hexamethylenediamine trimer in FIG. 5) was found to have improved processability and mechanical properties, making it an ideal binder candidate.

Figure 6:
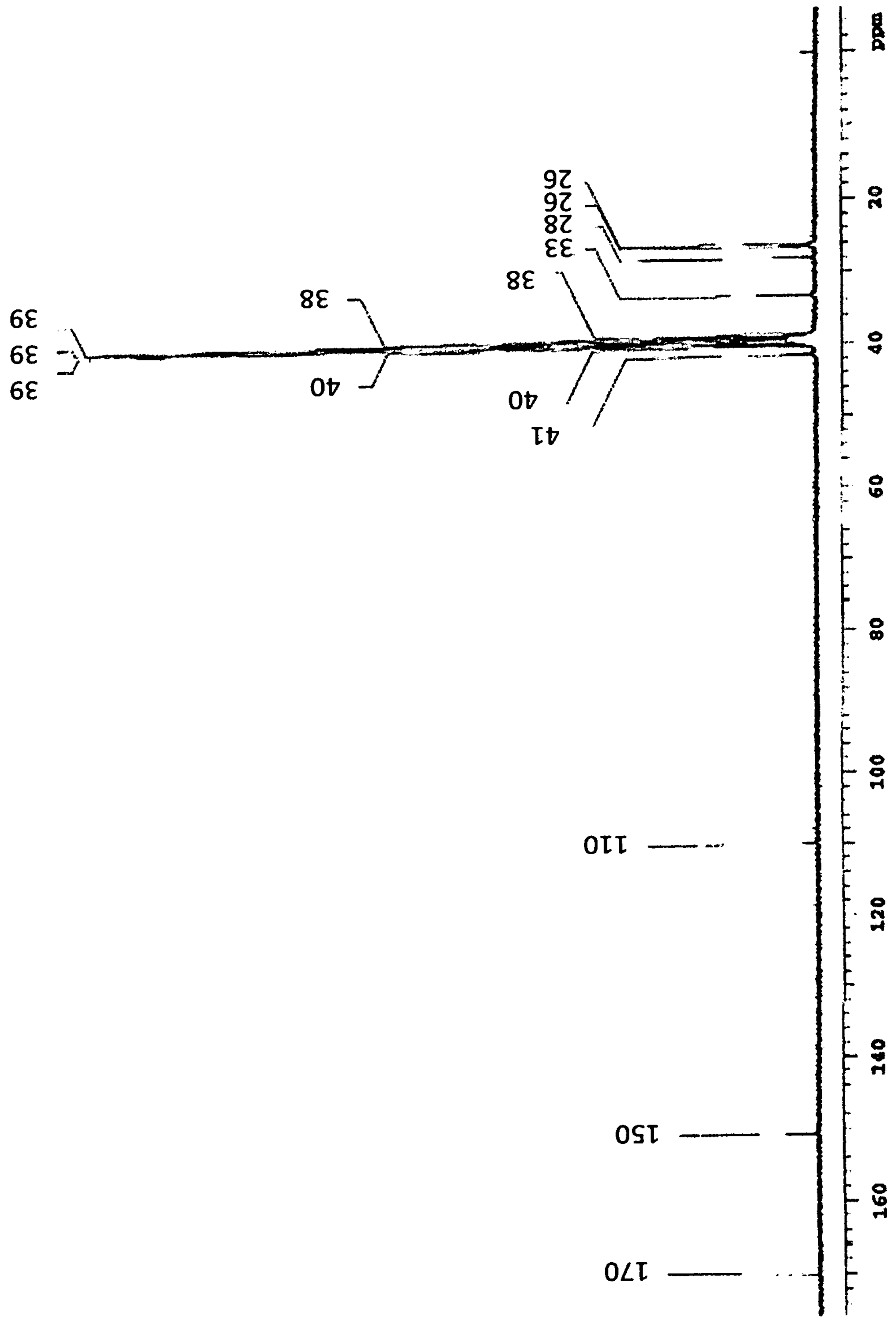
FIG. 6 is $^{13}$C NMR data for the hexamethylenediamine trimer (product D from FIG. 5)

NMR of the hexamethylenediamine trimer, shown in FIG. 6, helps confirm structure of the molecule. Chemical Shifts are 170, 150, and 110 ppm for the carbonyl carbon, the ipso carbon, and the four identical iodinated aromatic carbon atoms, respectively. Additionally, the hexamethylenediamine material had five methylene peaks at 41, 33, 28, 26.5, and 26.1 ppm. The sixth expected methylene peak is likely concealed by the DMSO heptamer.

Figure 7:
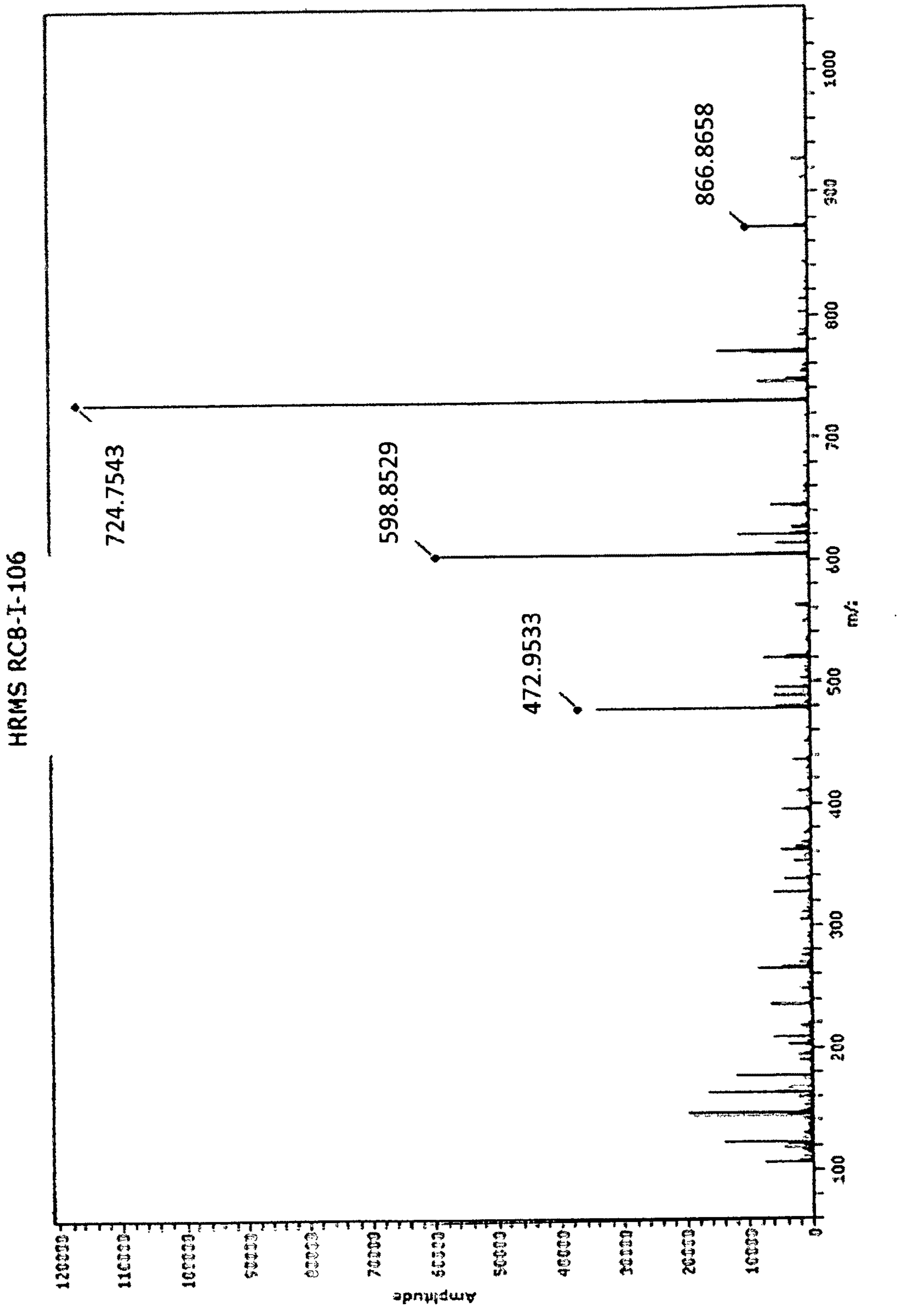
FIG. 7 is HRMS data for the hexamethylenediamine trimer (product D from FIG. 5)

High resolution mass spectrometry (HRMS) of the hexamethylenediamine trimer, shown in FIG. 7, aids in structural confirmation and isotopic identity of the material. Identified masses include the molecular ion plus hydrogen (866.8658 m/z), the molecular ion plus hydrogen with one of the amide groups cleaved (724.7543 m/z), 724 minus an iodine plus a hydrogen (598.8529 m/z), and 598 minus an iodine plus a hydrogen (472.9533 m/z). All masses were within the accepted 5% ppm error from theoretical values.

Figure 8:
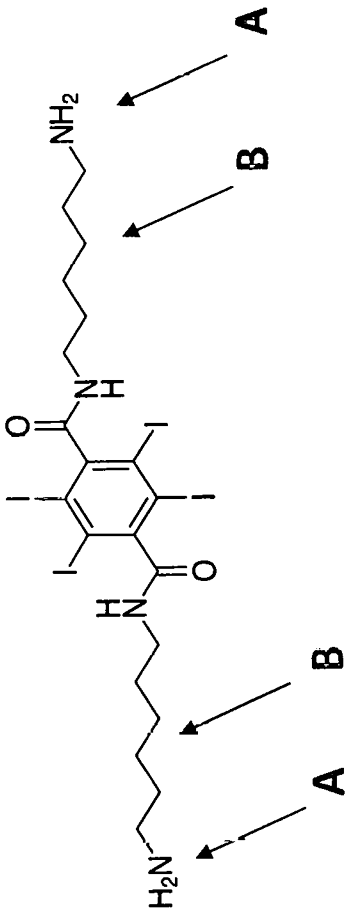
FIG. 8 illustrates the hexamethylenediamine trimer structure (product D from FIG. 5) (left) and its utility as a binder in pressed formulations (right). Left: Terminal amine groups (A) allow for crosslinking post formulation, and long aliphatic chains (B) give the material flexibility allowing for a press-able binder. Right: Pressed pellets containing a mixture of the hexamethylenediamine trimer, aluminum, and iron oxide.

The structure of hexamethylenediamine trimer to be used as a binder is shown in FIG. 8 (left). The long aliphatic chains (green B) make the material somewhat flexible producing a compactable white powder. This would be an ideal binder candidate for pressed formulations. This material was found to be press-able, and pressed mixtures with aluminum and iron oxide were prepared (right). Additionally, the terminal amine functionalities (red A) are highly nucleophilic and will allow the material to be end linked or cross-linked post formulation by any electrophilic linker group. Furthermore, both A and B functionalities improve the solubility of this material.

The hexamethylenediamine trimer is a promising binder candidate, however, the other iodinated polymeric materials described in this document may also be acceptable binders. Additionally, similar analogs derived from other diamines may also provide favorable binders.

The binder may be mixed with aluminum, or other metal fuel, and oxidizers, giving thermites, or other energized materials to produce an even stronger biocidal composition. In addition to the $Fe_2O_3$ thermite shown in FIG. 8, other thermite mixtures were also prepared in various ratios (Trimer with Al and: $Fe_2O_3$, CuO, $MoO_3$, $Bi_2O_3$, perfluorotetradecanoic acid, or $I_2O_5$), demonstrating these materials are highly tailorable for biological agent defeat applications. These materials are currently undergoing combustion characterization and select candidates will move forward to spore testing.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

It is to be understood that the foregoing description and specific embodiments are merely illustrative of the best mode of the invention and the principles thereof, and that various modifications and additions may be made to the invention by those skilled in the art, without departing from the spirit and scope of this invention, which is therefore understood to be limited only by the scope of the appended claims.

What is claimed is:

1. A polymer having biocidal substituents, comprising: an iodinated polymer, polyethylene tetraiodotere-phthalamide (PETITA), as shown below, and analogs thereof

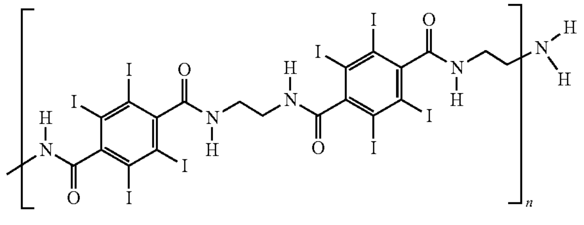

wherein said analogs are selected from the group consisting of hexamethylenediamine and other aliphatic, cycloaliphatic, and aromatic diamines.

2. The polymer according to claim 1, wherein said iodinated polymer entraps micron sized particles of at least one of aluminum, other metal fuels, and various oxidizers within the polymer matrix, and gives one of polymer-metal and polymer-thermite composites.

3. The polymer according to claim 2, wherein a layer of fluorinated compound is evaporatively coated on one of said iodinated polymer-metal and said polymer-thermite composite.

4. A polymer having biocidal substituents, comprising: either of the trimers below:

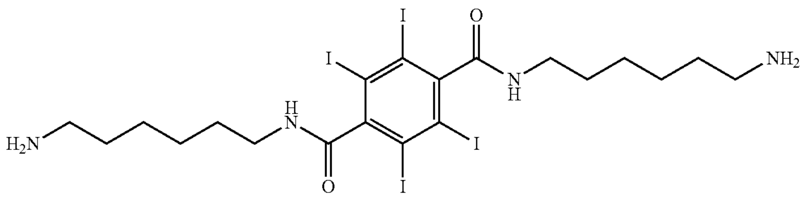 [SMILES: NCCCCCCNC(=O)c1c(I)c(I)c(C(=O)NCCCCCCN)c(I)c1I]

or

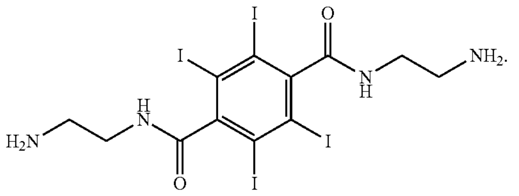 [SMILES: NCCNC(=O)c1c(I)c(I)c(C(=O)NCCN)c(I)c1I]

5. The polymer according to claim 1, wherein said iodinated polymer and said analogs are a trimer, and wherein said trimer is a binder for biological agent defeat formulations.

6. The polymer according to claim 1, wherein said iodinated polymer and said analogs are a trimer, wherein said trimer is a binder for biological agent defeat formulations, wherein the biological agent defeat formulations include an iodinated binder, metal fuel, and an oxidizer, wherein the metal fuel is micron aluminum particles, and wherein the oxidizer is selected from one of metal oxides, fluorinated compounds and iodine pentoxide.

7. A process for making one of a polymer or trimer of claim 1 or 4 having biocidal properties, comprising: dissolving stoichiometric amounts of tetraiodoterephthaloyl chloride, one of ethylene diamine and an analog of the ethylene diamine, and trimethylamine (TEA) into N-Methyl-2-pyrrolidone (NMP) in a dried Schlenk flask under argon atmosphere, wherein the analogs include hexamethylenediamine, and other aliphatic, cycloaliphatic, and aromatic diamines; stirring the Schlenk flask overnight at room temperature; diluting the mixture with water forming a slurry; collecting the slurry as a light yellow solid by vacuum filtration; washing the solid with ethanol and diethyl ether; and crushing the solid and drying it using a high vacuum for giving one of the polymer or trimer in a quantitative yield.

8. The process according to claim 7, wherein said tetraiodoterephthaloyl chloride is synthesized by the steps comprised of:

adding tetraiodoterephthalic acid and an excess thionyl chloride to a dried Schlenk flask connected to a reflux condenser and under argon atmosphere;

stirring and heating the Schlenk flask for 6 h at 100° C.;

removing by evaporation any unreacted thionyl chloride leaving impure tetraiodoterephthaloyl chloride;

dissolving the impure tetraiodoterephthaloyl chloride in anhydrous tetrahydrofuran (THF) to form a dissolved tetraiodoterephthaloyl chloride;

filtering the dissolved tetraiodoterephthaloyl chloride using a cannula tube;

evaporating the THF leaving a tan solid; and drying by high vacuum to obtain the tetraiodoterephthaloyl chloride in 75% yield.

9. The process according to claim 8, wherein said tetraiodoterephthalic acid (TIPA) is synthesized by the steps comprised of: dissolving terephthalic acid in 20% fuming sulfuric acid in a reaction flask, wherein the flask is vented to a sulfuric acid bubbler, stirred, and heated to a temperature of 100° C.; adding iodine to the reaction flask, and incrementally raising the temperature to 125° C. for 30 min, wherein the flask is wrapped in foil and the temperature is increased to 150° C. for 15 min, 170° C. for 15 min, and 190° C. for 6 h; allowing the reaction mixture to cool overnight; pouring the mixture into ice cold water, washing the flask therein forming a slurry having a pink solid, which is collected by vacuum filtration, wherein the pink solid is impure TIPA; purifying the TIPA by dissolving it in aqueous KOH to a pH of about 10, vacuum filtering, adding NaHSO3 to the filtrate, therein causing the TIPA to precipitate by the addition of concentrated HCl acid to a pH of about 1, vacuum filter the precipitate to dryness and allowing it to air dry overnight; and removing any remaining impurity by triturating the TIPA with acetone at room temperature and in hot methanol, and then vacuum filtering until the TIPA is a white solid at 45% yield.

10. A process for making one of a polymer or trimer of claim 1 or 4 having biocidal properties, comprising: dissolving stoichiometric amounts of tetraiodoterephthaloyl chloride, one of ethylene diamine and an analog of ethylene diamine, and trimethylamine (TEA) into N-Methyl-2-pyrrolidone (NMP) in a dried Schlenk flask under argon atmosphere, wherein the analogs include hexamethylenediamine and other aliphatic, cycloaliphatic, and aromatic diamines; stirring the Schlenk flask overnight at room temperature; diluting the mixture with water forming a slurry; collecting the slurry as a light yellow solid by vacuum filtration; washing the solid with ethanol and diethyl ether; and crushing the solid and drying it using a high vacuum to give at least one of the polymer or trimer in quantitative yield.

11. The process according to claim 10, wherein polymer-metal composites are prepared by trapping micron particles of aluminum within the polymer matrix of one of the polymer or trimer during the polymerization reaction.

12. The process according to claim 11, wherein the polymer-metal composites are coated with an evaporative layer of perfluoro compound.

13. The process according to claim 10, wherein metal oxides were added to the polymerization reaction with aluminum to produce iodinated polymer-thermite composites.

14. The process according to claim 10, wherein said trimers function as a binder for pressed thermite composites, which involve various oxidizers and metals being mixed in with the trimer and pressed into pellets to develop biological Agent Defeat formulations.

* * * * *